United States Patent
Reed

[11] Patent Number: 5,968,047
[45] Date of Patent: Oct. 19, 1999

[54] FIXATION DEVICES

[76] Inventor: Thomas Mills Reed, 29 Raintree Pl., The Woodlands, Tex. 77381

[21] Appl. No.: 09/110,507

[22] Filed: Jul. 6, 1998

Related U.S. Application Data

[63] Continuation of application No. 08/791,611, Jan. 31, 1997, Pat. No. 5,868,749, which is a continuation-in-part of application No. 08/627,355, Apr. 5, 1996, abandoned.
[60] Provisional application No. 60/027,510, Sep. 7, 1996.

[51] Int. Cl.[6] .................................................... A61B 17/56
[52] U.S. Cl. ................................ 606/76; 606/69; 606/72; 606/73
[58] Field of Search ................................ 606/69, 76, 77, 606/72, 73, 104

[56] References Cited

U.S. PATENT DOCUMENTS

| | | | |
|---|---|---|---|
| 3,739,773 | 6/1973 | Schmitt et al. | 128/92 |
| 4,356,572 | 11/1982 | Gullemin et al. | 128/92 |
| 4,632,100 | 12/1986 | Somers | 128/92 |
| 4,654,464 | 3/1987 | Mittelmeier et al. | 623/16 |
| 4,905,680 | 3/1990 | Tunc | 606/69 |
| 4,924,865 | 5/1990 | Bays et al. | 606/77 |
| 4,932,973 | 6/1990 | Gendler | 623/16 |
| 4,944,742 | 7/1990 | Clemow et al. | 606/59 |
| 4,976,715 | 12/1990 | Bays et al. | 606/77 |
| 4,997,433 | 3/1991 | Goble | 606/64 |
| 5,013,316 | 5/1991 | Goble | 606/72 |
| 5,019,038 | 5/1991 | Linden | 604/49 |
| 5,053,036 | 10/1991 | Perren et al. | 606/69 |
| 5,053,049 | 10/1991 | Campbell | 623/16 |
| 5,059,206 | 10/1991 | Winters | 606/213 |
| 5,084,050 | 1/1992 | Draenert | 606/77 |
| 5,108,399 | 4/1992 | Eitenmuller et al. | 606/77 |
| 5,112,354 | 5/1992 | Sires | 623/16 |
| 5,129,906 | 7/1992 | Ross et al. | 606/77 |
| 5,147,362 | 9/1992 | Goble | 606/72 |
| 5,167,664 | 12/1992 | Hodorek | 606/73 |
| 5,169,400 | 12/1992 | Mühling et al. | 606/73 |
| 5,217,462 | 6/1993 | Asnis et al. | 606/73 |
| 5,236,431 | 8/1993 | Gogolewski et al. | 606/77 |

(List continued on next page.)

FOREIGN PATENT DOCUMENTS

| | | |
|---|---|---|
| 471-334 | 2/1992 | European Pat. Off. . |
| 2-405-062 | 5/1979 | France . |
| 2-405-705 | 5/1979 | France . |
| 60-150756 | of 1985 | Japan . |
| 62-268553 | 11/1987 | Japan . |
| 2 148 122 | 5/1985 | United Kingdom . |
| 2 175 807 | 12/1986 | United Kingdom . |

OTHER PUBLICATIONS

Päivärinta et al., "Intraosseous Cellular Response to Biodegradable Fracture Fixation Screws Made of Polyglycolide or Polylactide", Archives OV Orthopaedic and Trauma Surgery, pp. 71–74, 1993.

Bucholz et al., "Fixation with Bioabsorbable Screws for the Treatment of Fractures of the Ankle", The Journal of Bone and Joint Surgery, vol. 76–A, No. 3, pp. 319–324, Mar. 1994.

(List continued on next page.)

*Primary Examiner*—Michael Buiz
*Assistant Examiner*—Julian Woo
*Attorney, Agent, or Firm*—Arnold, White & Durkee

[57] ABSTRACT

Sterile bone fixation devices, such as bone screws, pins, anchors and plates, fabricated from bone tissue and the method of making such devices.

71 Claims, 7 Drawing Sheets

U.S. PATENT DOCUMENTS

| | | |
|---|---|---|
| 5,275,601 | 1/1994 | Gogolewski et al. ............... 606/72 |
| 5,290,281 | 3/1994 | Tschakaloff ........................ 606/28 |
| 5,298,254 | 3/1994 | Prewett et al. ................... 424/422 |
| 5,306,304 | 4/1994 | Gendler ............................. 623/16 |
| 5,352,224 | 10/1994 | Westermann ...................... 606/61 |
| 5,360,450 | 11/1994 | Giannini ............................ 623/21 |
| 5,364,400 | 11/1994 | Rego, Jr. et al. .................. 606/72 |
| 5,370,662 | 12/1994 | Stone et al. ...................... 606/232 |
| 5,403,348 | 4/1995 | Bonutti ........................... 606/232 |
| 5,417,533 | 5/1995 | Lasner ............................. 411/426 |
| 5,417,712 | 5/1995 | Whittaker et al. ................. 606/72 |
| 5,439,684 | 8/1995 | Prewett et al. .................... 623/16 |
| 5,443,482 | 8/1995 | Stone et al. ...................... 606/232 |
| 5,464,426 | 11/1995 | Bonutti ........................... 606/232 |
| 5,464,439 | 11/1995 | Gender ............................ 623/111 |
| 5,466,243 | 11/1995 | Schmieding et al. .............. 606/16 |
| 5,470,334 | 11/1995 | Ross et al. ........................ 606/72 |
| 5,496,348 | 3/1996 | Bonutti ........................... 606/232 |
| 5,507,813 | 4/1996 | Dowd et al. ...................... 623/16 |
| 5,522,846 | 6/1996 | Bonutti ........................... 606/232 |
| 5,527,343 | 6/1996 | Bonutti ........................... 606/232 |
| 5,534,011 | 7/1996 | Greene, Jr. et al. .............. 606/232 |
| 5,534,012 | 7/1996 | Bonutti ........................... 606/232 |
| 5,569,250 | 10/1996 | Sarver et al. ..................... 606/69 |
| 5,569,252 | 10/1996 | Justin et al. ...................... 606/73 |
| 5,584,836 | 12/1996 | Ballintyn et al. .................. 606/73 |
| 5,585,116 | 12/1996 | Boniface et al. ................. 424/549 |
| 5,601,557 | 2/1997 | Hayhurst .......................... 606/72 |
| 5,601,558 | 2/1997 | Torrie et al. ...................... 606/72 |

OTHER PUBLICATIONS

Lavery et al., "Mechanical Characteristics of Poly–L–Lactic Acid Absorbable Screws and Stainless Steel Screws in Basilar Osteotomies of the First Metatarsal", The Journal of Foot and Ankle Surgery, vol. 33, No. 3, pp. 249–254, 1994.

Malinin et al., "Healing of Fractures with Freeze–dried Cortical Bone Plates", Clinical Orthopaedics and Related Research, No. 190, pp. 281–286, Nov. 1984.

Johnson & Johnson Orthopaedics, "OrthoSorb 2.0mm Absorbable Pin with Applicator Kit", 1992.

Mitek Surgical Products, Inc., "Fastout", 1996.

Corey et al., "Principles of Internal Fixation", Comprehensive Textbook of Foot Surgery, 2nd Ed., pp. 113–159 (1992).

Mahan, "Bone Grafting", Comprehensive Textbook of Foot Surgery, 2nd Ed., pp. 1232–1255 (1992).

Musculoskeletal Transplant Foundation, "Musculoskeletal Allograft Tissue", Aug. 1990.

Synthes (USA), "3.0 mm Cannulated Screw and Threaded Washer Technique Guide", 1996.

Fixation Plates, Manual of Internal Fixation, Springer–Verlag Berlin Heiderburg New York, 1979, pp. 18–20, 46–49, 293.

"Factors Affecting Clinical Results", pp. 7–8.

Santavirta, "Immune Response to Polyglycolic Acid Implants", Journal Bone Joint Surgery, vol. 72–B, No. 4, p. 597, Jul. 1990.

Yen, et al., "The Biofix Absorbable Rod," Journal of the American Podiatric Medical Association, vol. 81, No. 2, pp. 62–67, Feb. 1991.

Howmedica Inc, "Mainstay Soft Tissue Anchor," 1996.

Bioscience Inc., "Biofix Bioabsorbable Implants".

Goldberg et al., "The Biology of Bone Grafts", Seminars in Arthroplasty, vol. 7, No. 1 (Jan.), 1996: pp. 12–17.

Nolan et al., "Living Bond Grafts: Cell Culture May Overcome the Limitations of Allografts", British Medical Journal, Jun. 13, 1992 p. 1520.

Buckwalter et al., "Bone Biology", The Journal of Bone and Joint Surgery, vol. 77–A, No. 8, Aug. 1995.

Albee, Fred H., "Bone Graft Surgery in Disease, Injury and Deformity", D. Appleton–Century Company Incorporated, New York and London, 1940, p. 30 Fig. 21, and p. 216 Fig. 157, pp. 212–216.

Albee, Fred H., "Bone Graft Surgery in Disease, Injury and Deformity", D. Appleton–Century Company Incorporated, New York and London, 1940, pp. 18–47.

Albee, Fred H., "Bone Surgery with Machine Tools", Scientific American, Apr. 1936, pp. 178–181.

Albee, Fred H., "The Improved Albee Bone Mill", The American Journal of Surgery, Mar. 1938, pp. 657–660.

Albee, Fred H., "Bone Graft Surgery", W. B. Saunders Company, Philadelphia and London, 1917, pp. 52–63, 212–213, 221–240.

FIXATION DEVICES

The present application claims priority from both provisional application 60/027,510 filed Sep. 7, 1996 entitled "Bone Fixation Devices" filed Oct. 7, 1996 and as a continuation of application Ser. No. 08/791,611, filed Jan. 31, 1997, now U.S. Pat. No. 5,868,749, which is a continuation-in-part of U.S. patent application Ser. No. 08/627,355, filed Apr. 5, 1996 now abandoned.

BACKGROUND OF THE INVENTION

1. Field of the Invention

This application relates to fixation devices. More particularly, it relates to bone fixation devices made from bone tissue, bone powder, and related natural material.

2. The Prior Art

In repairing bone fractures or breaks and in other bone repair, it is customary to use pins, nails or screws to hold the bone together to allow regrowth and healing. Such screws, pins and other fixation devices are customarily constructed of metal, e.g. surgical stainless steel, or polymeric materials. Resorbable polymers have found wide use in recent years. Polyglycolide, polydioxanone and polylactide polymers, polymers that are also used in absorbable suture materials, have been successfully used. Such fixation devices come in various shapes and sizes, each designed to provide some special benefit. For example, U.S. Pat. No. 5,417,533 provides a bone screw having a helical thread that gradually increases in thickness from the tip to the head of the screw. This screw design is said to increase the screw's resistance to tearing out of the bone and have the further advantage of being inserted with minimum tearing or cracking of the bone.

AO/ASIF or Arbeitgemeinschaft fur Osteosynthesisfragen (English translation, Association for the study of Internal Fixation[ASIF]) screw designs are commonly and widely used. Screw fixation devices are generally inserted into pre-drilled and tapped holes in the bone or cartilage to be repaired. Pins are used where appropriate. Pins are, of course, distinguished from screws by the lack of threads and leads and are more commonly used to provide rigidity to bone rather than compression. Fixation plates are used to hold bone or other skeletal parts into place. The plates are usually held in place by screws. Anchors are also used which provide an attachment for sutures in the body.

Metal fixation devices and absorbable polymer devices are not without problems. Metal pins and screws often need to be removed, causing additional trauma to the patient and causing weakening of the repaired bone. One advantage of the polymer devices is elimination of the need to remove the device when the bone has healed. However, the long-term consequences of polymer absorption are not known. Moreover, absorbable polymers can cause irritation and sterile abscess from the decomposition products of the polymer.

Bone grafting is also well known. Grafting is the process in which live or nonliving bone is placed between or into living bone in the body. The graft becomes incorporated into the renewed bone structure of the living bone as it replaces itself and regrows. New bone growth replaces the graft and eliminates the graft material over time whether the graft is of nonliving or live bone tissue. Freeze dried sterile bone is most often used. When cortical bone is used in grafts the absorption of the graft material takes a long time, usually months. For cancellous bone grafts the absorption is often effected in days or weeks. Heretofore, bone fixation and bone grafting have been separate operation. Fixation is the holding of bone in place for healing and grafting is the provision of a bone structure for regrowth of new bone.

I have now discovered that the disadvantages of the present steel and/or polymer fixation devices can be obviated by use of fixation devices made from bone tissue. Moreover, the fixation device is, in effect, grafted into the bone in which it is used and does not require subsequent removal. For human use, human bone tissue is used. For veterinary use, appropriate animal bone or human bone tissue is used. Human bone tissue is readily available from a number of "Bone Banks". These bone banks provide suitable bone tissue that has been cleaned and sterilized for human therapeutic use, such as in bone grafts and the like.

SUMMARY OF THE INVENTION

This invention relates to a fixation device adapted to be grafted into a biologically active structure. The fixation device is interactive with the biological structure and actually becomes a part of the biological structure. Unlike the prior art, the fixation device of this invention is non-metallic, and is not biologically toxic. Further, the fixation device is compatible with the functional characteristics of the biologically active structure.

The fixation device can be made from naturally occurring bone tissue, preferably human or animal cortical bone tissue. In one embodiment of the invention, a bone fixation device is fashioned from donor bones obtained from cadavers or other suitable sources, such as animals. Typically the bone fixation device of this invention takes the physical form of a screw, a pin, a plate, an anchor, a cannulated screw, or other physical form adapted to meet the specific bone repair function.

In one embodiment, the fixation device is formed in the shape of a screw. The screw has a head portion that is functionally adapted to provide rotational movement to the device. The fixation device also has a longitudinal portion that is fixedly attached to the head portion. This longitudinal portion also has a means for fixedly retaining a portion of the device in a biologically active structure.

Another embodiment containing the screw is an assembly comprising 1) a bone screw made from bone tissue and 2) a surgical steel adapter having a fitting on one end that meshes with a bone screw head, in which fitting and screw head are spherical with at least two flat sides, or is nonspherical and has at least three flat sides. On the other end of the adapter is a hexagonal recess adapted to mesh with a standard AO/ASIF driver or Philip's driver. The invention is also a kit comprising an adapter and screw made from bone tissue. The invention is also the method of making such devices by machining or otherwise fashioning the device from sterile bone and subjecting the fabricated device to sterilization treatment to render it sterile and immunologically acceptable.

In another embodiment of the invention, a cannulated screw is formed from bone material. The cannulated screw has two end portions, at least one of which is adapted to provide rotational movement to the device and has at least two or at least three flat sides. The two end portions are fixedly attached to a longitudinal body portion, which has a means for fixedly retaining at least a portion of the device in a biologically active structure. The cannulated screw also has an aperture extending along the entire longitudinal axis of the screw to permit insertion of guide means, such as a pin or wire, for use during application or insertion of the screw. In certain preferred embodiments, the aperture can be threaded or have an internal configuration that facilitates its ultimate end use. The cannulated screw of this invention may be either the short thread or long thread configuration. In one cancellous screw embodiment of this invention the thread profile is 3.0 mm thread diameter, 1.9 mm core diameter, and 1.25 pitch. These dimensions are provided by way of illustration and not limitation.

In still another embodiment of this invention, the bone fixation device is in the form of a bone anchor. The anchor is a screw-like device, which has a head fixedly attached to a longitudinal body portion. The head can provide rotational movement to the device. The longitudinal body portion is at least partially threaded. These threads secure the bone anchor to the bone of the patient. The anchor has one or more apertures or openings extruding through one or more sections of the width of the anchor member, typically the head portion of the anchor. The anchor embodiment can be used in a variety of sizes and thread pitches depending on the patient and ultimate end use. For example, common anchor sizes include, 2.7 mm×8.0 mm; 3.5 mm×10.0 mm; and 4.5 mm×12.0 mm (outer diameter ×length). These sizes are provided by way of illustration and not limitation. When in place the aperture in the anchor head permits use of these devices in combination with other body repair devices such as suture thread for ligament or tendon repair and attachment to bone.

In still a further embodiment of this invention, the bone fixation device is provided in the form of a plate. The plate can be formed of either one or more pieces of bone formed into the desired shape or can be molded from bone powder in combination with an appropriate adhesive material. The bone plates can take a variety of forms and shapes depending on the desired end use. Typically, the bone plates take the form of a small-T or an oblique-L shape.

Other physical shapes of the bone plate include a tubular (straight) section, a clover-leaf section and any other physical size and form desired. Common to all the bone plate embodiments is the incorporation of a series of screw holes to permit anchoring of the bone plate onto the receptor surface.

In the bone plate embodiment of this invention in which a bone powder is used, the powder is adhered into the desired shape by the incorporation of a bonding agent into the powder mix. Such bonding agent may be absorbable polymers, a resorbably glass/ceramic composites.

In still another embodiment of this invention a pin is used as the bone fixation device. The primary distinction between a pin and screw is that the pin is not adapted to provide compression after insertion into the bone or other receptive surface. The longitudinal surface of the pin can be threaded, may contain barbs, may be smooth, or may contain spikes. It is essential that the pin not provide compression but merely provide alignment.

In still another embodiment of this invention the pins, screws, anchors, and plates that are used as the fixation devices of this invention may be perforated to enhance incorporation in the host biological structure. The perforations may be of any functionally desired size and density.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

This invention is bone fixation devices made from bone tissue. Heretofore, bone fixation devices have been made from material foreign to the body. Metal devices generally need to be removed and polymer devices decompose and the decomposition products are absorbed by the body. The devices of this invention, being made from bone tissue, fiction like a bone graft and are integrated and, at least partially absorbed into the body in the same manner as other bone graft material. The devices may be made in the same design as existing metal or polymer devices except that they are fabricated from sterile bone tissue. Suitable bone tissue material is described below. The device, as in a bone screw embodiment, is made from bone tissue under conditions that are either aseptic or at least sufficiently clean that the completed device can be sterilized for use. For example, a screw made of sterile bone tissue, is machined under clean conditions with a sufficiently sharp cutting tool and under cooling conditions to prevent burning of the bone tissue. The completed screw is then sterilized by boiling, autoclaving and/or by treatment with hydrogen peroxide, ethylene oxide or other suitable materials known to the art. The device may also be irradiated if necessary. Typically, aseptic bone tissue is frozen, freeze dried or demineralized for long-term storage. Freeze drying is a very convenient form for bone tissue useful for this invention. Freeze drying increases shelf life of the tissue and allows a convenient form for fabrication. Typically the frozen or freeze dried material is sealed under vacuum for storage prior to use.

Bone Tissue

Bone is skeletal tissue that, when living, contains living cells embedded in a hard matrix. This matrix consists mostly of calcium phosphate (as hydroxylapatite) and other calcium minerals, held together by collagen (a protein) and other organic substances. Two major types of bone tissue exist. Compact, or cortical, bone tissue has many rod-like Haversian systems, each containing many concentric cylindrical layers (lamellae) surrounding a central blood vessel. Between these layers the bone cells (osteocytes) lie within irregular spaces called lacunae. Tiny pores (canaliculi) connect the osteocytes with one another and with the central blood vessel, allowing oxygen and nutrients to reach the cells.

Cancellous, or spongy, bone tissue has a loose network of rigid beams (trabeculae). The spaces between these trabeculae contain marrow, a blood-forming tissue. Bone tissue renews itself throughout life, constantly tearing down and rebuilding its mineralized framework. Chemical factors secreted by immune-system cells apparently regulate the balance between bone resorption and formation. Bone-absorbing cells (osteoclasts) dissolve old tissue, and bone-forming cells (osteoblasts) deposit new tissue. New trabeculae and new Haversian systems are generally oriented parallel to the direction of greatest stress. Once bone tissue hardens, the osteoblasts change into mature osteocytes.

Bones can be long, short (wrist bones), flat (many skull bones), irregular (vertebrae), or sesamoid (kneecap). Most limb bones are long and roughly cylindrical. The shaft (diaphysis) consists of compact bone surrounding an interior (the medullary cavity) or spongy bone and marrow. The ends (epiphyses) are mostly spongy bone tissue, capped by cartilage at the joints. Clavicle (collarbone) and many skull bones are called dermal bones because they ossify directly within the connective tissue of the skin (intramembranous ossification). Most other bones are endochondral, meaning that they form first as cartilage. Bone tissue replaces the cartilage during endochondral ossification. Bone tissue suitable for this invention are the compact or cortical bone and preferably the shaft of long endochrondral bones. Especially preferred are "cortical struts" from femoral cross section of bone. The bone tissue must be clean and sterile and immunologically compatible with the patient. Allogeneic (dead) bone that has undergone treatment to reduce antigenicity and to ensure sterility is available from "Bone Banks". Such bone tissue may be frozen, demineralized or freeze dried. For this invention freeze dried bone tissue is preferred. Frozen bone, usually stored in liquid nitrogen (at −196° C.) can be used but it is not usually practical to manufacture under conditions that will maintain the frozen state. Freeze dried bone tissue can be stored indefinitely under vacuum. Freeze drying also reduces antigenicity. Compressive and tensile strength of the bone is not seriously impaired by freeze drying.

Sterile bone is ensured by careful screening of donors and by proven harvesting and sterilization techniques. Selection of appropriate human donors is preferably based on medical guidelines developed by the American Association of Tissue Banks. Sterile bone tissue is obtained by acquiring it under sterile conditions or by careful preparation. Alternatively, bone is harvested under clean, but not necessarily sterile conditions and treated to achieve sterility. Ethylene oxide has been used, usually followed by freeze drying for suitable time to achieve a reduction in the ethylene oxide to acceptable levels. Such treated bone tissue may also be irradiated to improve sterility. Bone from the Musculoskeletal Transplant Foundation (MTF) of 960 Holmdel Road, Holmdel, N.J. is very suitable. MTF bone is recovered and processed under strict sterile conditions and is not treated with ethylene oxide nor irradiated. MTF donors undergo comprehensive screening to ensure against disease transmission.

For veterinary use, bone tissue is harvested from cortical bone tissue of the animal species that the bone screw is to used in or may be from the bone of other animals or may even be human bone. For example, for a screw used in repairing a fracture in a horse, horse bone may be used. Harvesting and sterilization is conducted in a manner to ensure that the device can be cleaned and sterilized after fabrication and prior to use.

Bone banks for animal bone are not available, but sterilization techniques used for human bone tissue are appropriate.

DESCRIPTION OF DEVICES OF THE INVENTION

Figure 1:
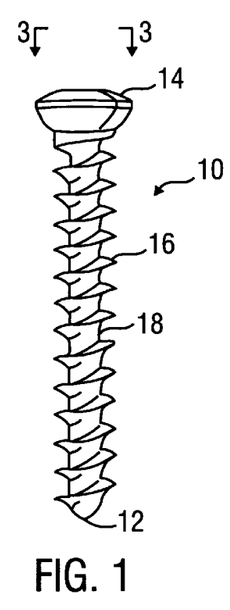
FIG. 1 is a side view of a standard AO/ASIF cancellous screw of this invention with threads extending from the pointed tip to the head.

AO or Arbeitgemeinschaft fur Osteosynthesisfragen (English translation, Association for the study of Internal Fixation [ASIF]) have standardized bone screw design. An example of the shape of an AO/ASIF screw is shown in FIG. 1. The size and function of the AO/ASIF design lends itself to compression fixation of dense or cortical bone fractures. These designs together with appropriate drivers and drills that match the screws are widely used in Orthopedic surgery. In the AO/ASIF system there is primarily used two types of screws: fully threaded screws for attaching cortical bone and partially threaded screws for attaching cancellous bone to cortical bone.

Short "cancellous" screws (screws used to connect cancellous bone) are usually fully threaded. FIG. 1 illustrates one embodiment of the present invention, a fully threaded cancellous bone screw 10. One end of the bone screw 10 has a point 12. The other end of the bone screw 10 has a screw head 14. The fully threaded bone screw 10 has threads 16 extending from the point 12 to the base of the screw head 14. The threads 16 protrude from a longitudinal core 18.

Figure 2:
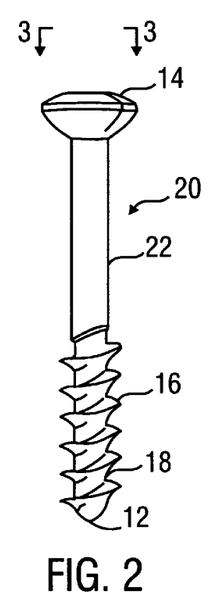
FIG. 2 is a side view of the same cancellous screw as shown in FIG. 1 with the exception that the threaded portion extends up only a portion of the longitudinally axis.

Cancellous bone screws may also be partially threaded. FIG. 2 illustrates a partially threaded cancellous bone screw 20. One end of the partially threaded bone screw 20 has a point 12 while the other end has a screw head 14. The partially threaded cancellous bone screw 20 has threads 16 only on the distal portion of the bone screw 20, whereas the proximal shaft 22 is smooth. The partially threaded bone screw 20 has threads 16 extending from the end that is a point 12 to a region below the screw head 14. The partially threaded cancellous bone screw 20 is used by drilling a passage in the proximal bone to allow the threads 16 or unthreaded screw shaft 22 to pass without significant contact into a tapped hole in the far bone. Once the threads 16 have crossed a fracture line, the screw shaft 22 is able to guide through the proximal fragment of bone.

Figure 3:
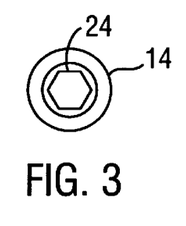
FIG. 3 is a top view of the head portion of the cancellous screws of FIGS. 1 and 2 showing the mechanism for applying a rotational force to the screws.
Figure 4:
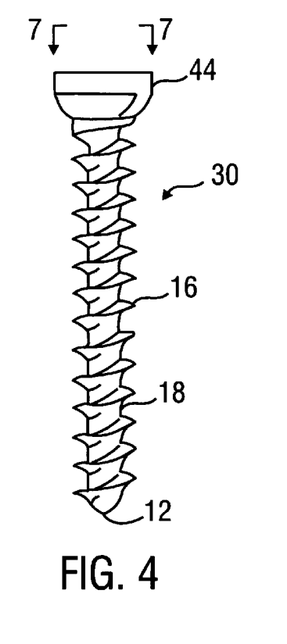
FIGS. 4 and 5 are cancellous screws similar to those shown in FIGS. 1 and 2 with the exception that the head portion has a different configuration for providing rotational movement to the screws.
Figure 8:
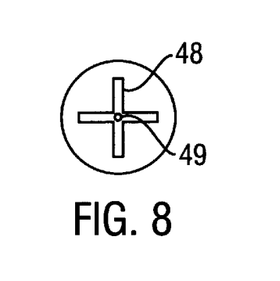

FIG. 3 illustrates the top view of a standard AO/ASIF screw head 14 of the cancellous screws of FIGS. 1 and 2. In standard AO/ASIF design, the screw head 14 may have a hexagonal recess 24 or a cruciform recess 48 with a centering hole 49 that provides implementation-to-screwdriver contact (FIG. 8). The hexagonal recess 24 is used in the screw head 14 for a more secure insertion and contact of the screwdriver with the screw head 14. The hexagonal recess 24 and stud-type screwdriver configuration provides a large contact surface between the screw head 14 and the driver that obviates the need for axial pressure to affect a controlled insertion or removal of the bone screw. In standard AO/ASIF screw sets, the AO/ASIF screw set comprises of the screw, appropriately sized drill tap and driver.

Figure 5:
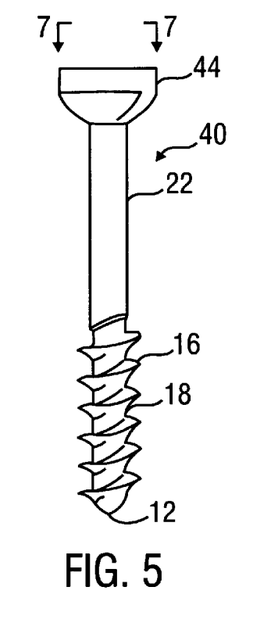
Figure 6:
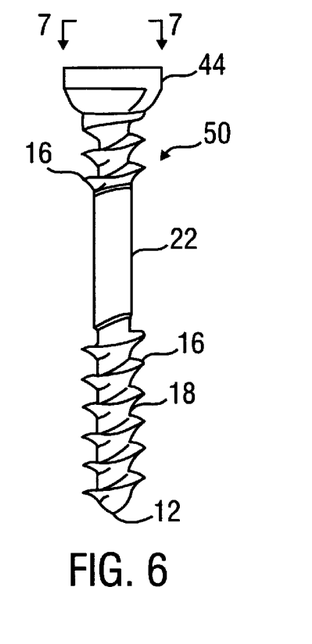
FIG. 6 is a side view of the same cancellous screw as shown in FIG. 5 with the exception that threads appear on both the proximal and distal portions of the longitudinal body.
Figure 7:
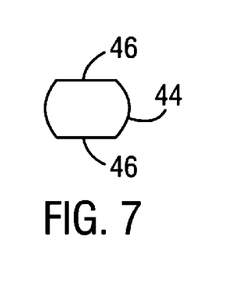
FIGS. 7, 8, 9, 10, and 11 are various top views of various head configurations that can be used to provide rotational movement to the screws, pins, or other fixation devices of this invention.
Figure 9:
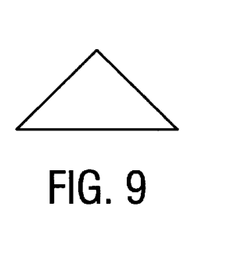
Figure 10:
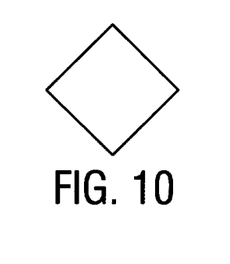
Figure 11:
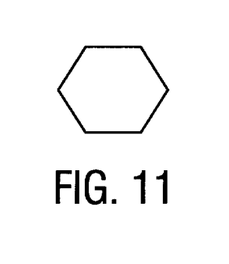

While the screws and/or pins of the present invention may have a variety of configurations known in the art, it is preferred that screws have the shape, dimensions and thread characteristics of the standard AO/ASIF design but with additional modification of the head as design parameters dictate. It is preferred that screws made according to this invention have the thread and shape of AO/ASIF screws but may have a spherical head 44 as shown in FIGS. 4, 5, 6 and 13. The spherical head 44 comprises of a cylinder with flat surfaces 46 on at least two opposing sides as shown in FIGS. 7 and 14. Similarly, the screw head may be non-spherical with at least three flat sides (FIGS. 9–11). The screw head may be of any shape that allows a driver (having a recess the shape of the head cross section) to achieve sufficient contact to prevent stripping of the head when the screw is driven into bone. Alternatively, the screw head can have a slot, perpendicular to the longitudinal body, that is adapted to receive a rotational tool. Additionally, the screw head can have an indention, perpendicular to the longitudinal body portion, that is adapted to receive a Philip's screwdriver. These are provided by way of illustration and not limitation. As with AO/ASIF screws, the underside of the screw head should have a spherical contour to create consistent and even pressure at the contact surface. Such spherical contour is shown on the underside of the screw heads in FIGS. 1, 2, 4, 5, 6 and 13. The screw head is slightly larger than the shaft of the screw at a point immediately above the top of the screw shaft.

It is preferred that the bone screws made according to this invention have threads that are the shape, dimensions and characteristics of the standard AO/ASIF design but may also have other thread patterns. The following table list some common dimensions of AO screws.

| ASIF Screw Sets (mm) | | | | |
|---|---|---|---|---|
| Thread Diameter | Head Diameter | Shaft diameter | Core diameter | Thread Pitch |
| 1.5 full thread | 3.0 mm | | 1.0 mm | |
| 2.0 full thread | 4.0 mm | | 1.5 mm | |
| 2.7 full thread | 5.0 mm | 2.5 mm | 1.9 mm | |
| 3.5 full thread | 6.0 mm | 2.5 mm | 2.4 mm | 1.25 mm |
| 4.0 partial thread | 6.0 mm | 2.5 mm | 1.9 mm | 1.75 mm |
| 4.0 full thread | 6.0 mm | 2.5 mm | 1.9 mm | 1.75 mm |
| 4.5 full thread | 8.0 mm | 3.0 mm | 3.0 mm | |
| 4.5 full thread | 8.0 mm | 3.0 mm | 3.0 mm | |
| 6.5 partial thread | 8.0 mm | 3.0 mm | 3.0 mm | |

The diameter of the screw heads range from 1 to 12 mm, 2 to 10 mm, or preferably 3 to 8 mm. Miniscrews have a screw head diameter of 1.5 to 2.0 mm. The core of the screw (the smallest diameter in the threaded section of the screw) is smaller than the thread diameter and may be slightly smaller than the shaft (the unthreaded section) of the screw. The thread diameter ranges from 1 to 8 mm. The core diameter ranges from 1 to 8 mm. For screws used to connect cancellous bone (cancellous screws) the screw may be threaded the entire length for screws of short length (FIGS. 1 and 4) or partially threaded for longer lengths (FIGS. 2, 5 and 6). Screws for connecting cortical bone are preferably threaded the entire length of the screw shaft (FIG. 13).

Figure 12:
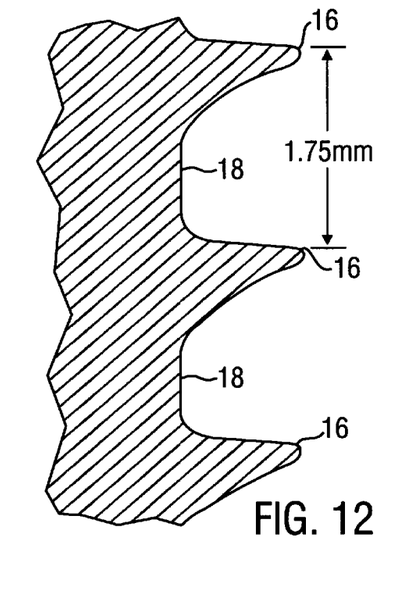
FIG. 12 is a diagrammatic view of the 1.75 mm pitch of a cancellous screw of this invention.

The threads will be from about 0.1 to 5 mm, 0.5 to 4 mm or preferably 1 to 3 mm point to point. The thread pattern is asymmetrical, with the compression side of the thread flat and relatively perpendicular to the core. FIG. 12 illustrates the diagrammatic view of the threads 16 and core 18 in one embodiment for the cancellous bone screws shown in FIGS. 4, 5 and 6. For example, a cancellous bone screw having a thread 16 diameter of about 4.0 mm will have a 1.75 mm pitch (pitch is distance from thread point to point on adjacent threads).

Figure 13:
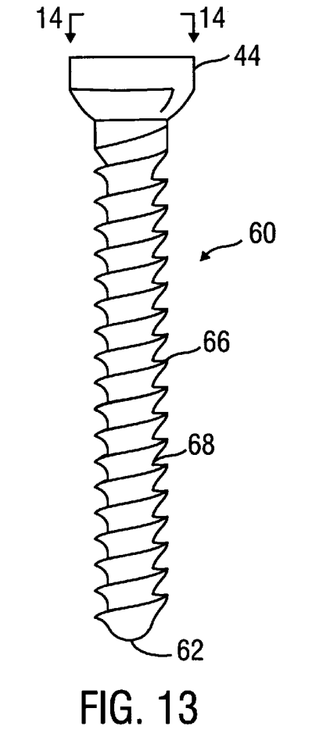
FIG. 13 is a side view of a cortical screw of this invention with threads running from the tip to the head portion.
Figure 14:
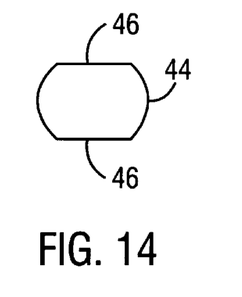
FIG. 14 is a top view of the head portion of the cortical screw shown in FIG. 13.
Figure 15:
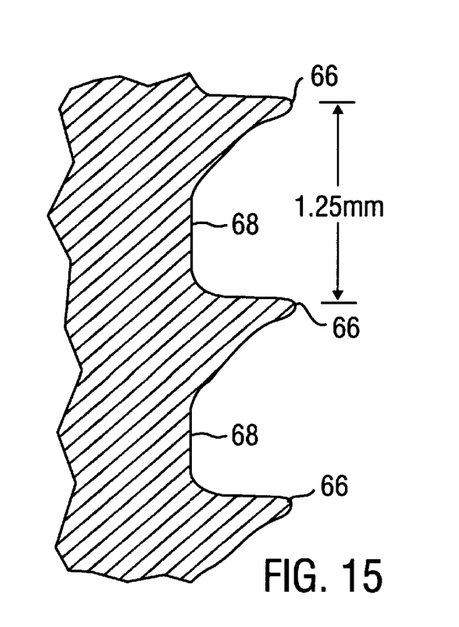
FIG. 15 is a diagrammatic view of the 1.25 mm pitch of a cortical screw of this invention.

FIG. 13 illustrates one embodiment of a cortical bone screw 60. Preferably, a cortical bone screw 60 has threads 66 protruding from a longitudinal core 68 and extending from point 62 to the base of the spherical head 44. FIG. 14 illustrates a top view of the spherical head 44 of the cortical bone screw 60. Like the cancellous bone screws 30, 40 and 50, the spherical head 44 comprises of a cylinder with flat surfaces 46 on at least two opposing sides. Similarly, the screw head may also be non-spherical with at least three flat sides (FIGS. 9–11). A cortical bone screw 60, however, has smaller threads 66 which are closer together than cancellous bone screw threads 16. For example, FIG. 15 illustrates the diagrammatic view of the threads 66 and core 68 in one embodiment for a cortical bone screw 60. A cortical bone screw 60 having a thread 66 diameter of about 3.5 mm will have a 1.25 mm pitch.

Figure 16:
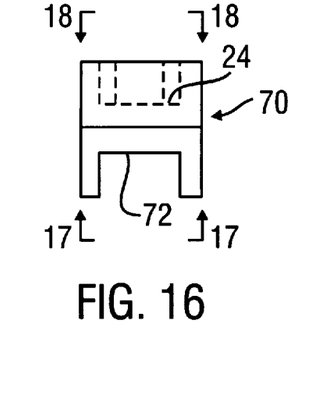
FIGS. 16, 17, 18, and 19 are an assortment of views of the adapters useful in this invention for providing rotational movement to the screws and pins of this invention. A single adapter may include one or more configurations, typically one on each end of the adapter.
Figure 17:
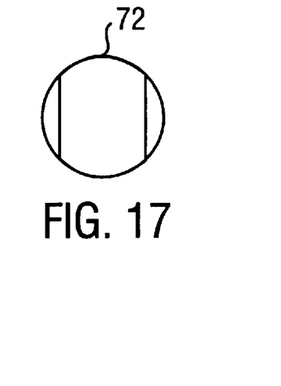
Figure 18:
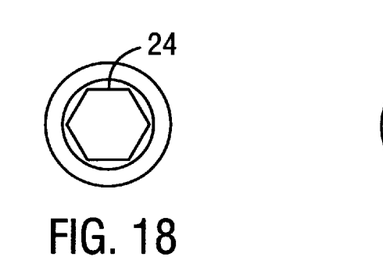
Figure 19:
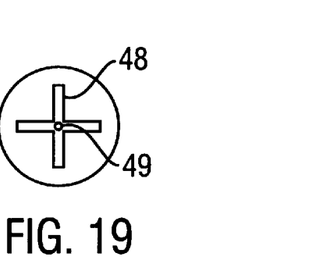

FIGS. 16, 17 and 18 illustrate three views of a head adapter 70 made of surgical steel. The head adapter 70 has a recess 72 that meshes with the spherical head 44 on one end and a standard AO/ASIF hexagonal recess 24 on the other end. Alternatively, the recess 72 may be replaced with a recess that meshes with a non-spherical head with at least three flat surfaces (FIGS. 9–11). Additionally, the AO/ASIF hexagonal recess 24 may be replaced with a cruciform recess 48 (FIG. 19). In one embodiment of this invention, there is provided an assembly, that comprises, 1.) the bone screw with the spherical head 44 that has at least two flat surfaces 46 or a non-spherical head with at least three flat surfaces (FIGS. 9–11), and 2.) a head adapter 70. This is illustrated by the combination of the bone screws in FIGS. 4, 5, 6 and/or 13 with the head adapter 70 in FIG. 16.

The head adapter 70 allows the use of AO/ASIF drivers and other instruments with the bone screws of this invention. The head adapter 70 is made in a variety of sizes. In one embodiment, the bone screw has a spherical head 44 diameter in the range of 1 to 8 mm, a length of 0.1 to 20 cm, and the head adapter 70 has a diameter in the range of 1.5 to 10 mm. In the preferred embodiment, the head adapter 70 is of a diameter of 1.25 to 1.5 mm, and the diameter of the spherical head 44 is also 1.25 to 1.5 mm. The length of the head adapter 70 is preferably 1 to 6 times the diameter of the screw shaft 22. This assembly may be provided in a kit form, comprising of a bone screw made of bone tissue having a spherical head 44 or a non-spherical head with at least three flat sides and a head adapter 70 sized to fit the bone screw. One such kit will comprise a bone screw having a 3.0 mm diameter screw head and a head adapter 70 having a 3.0 mm diameter.

Figure 20A:
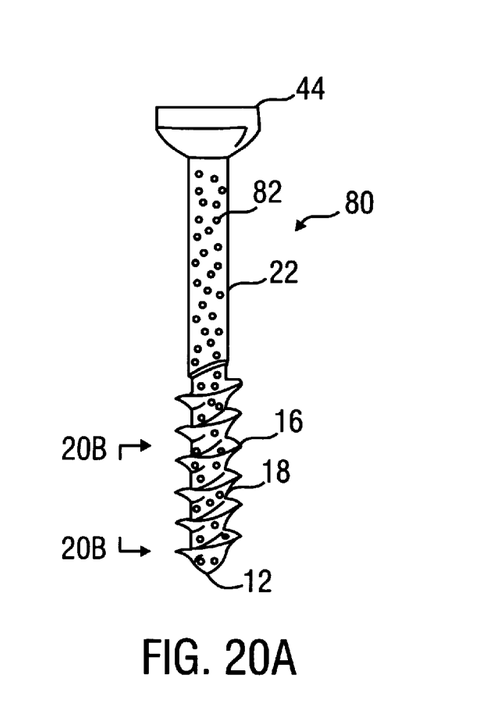
FIGS. 20A and 20B are a side view and an accompanying exploded view showing perforations on the threaded screw of FIG. 5.
Figure 20B:
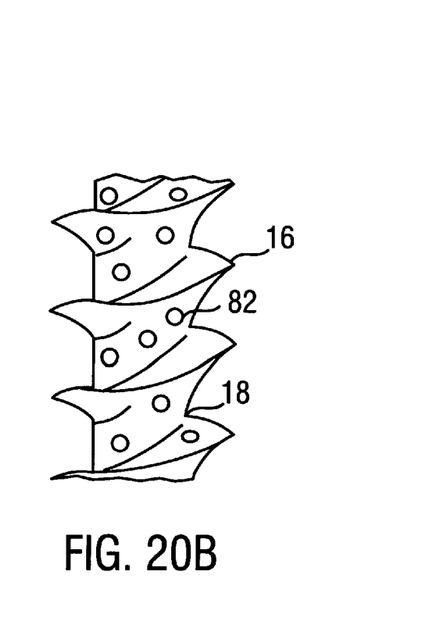

FIG. 20A illustrates one embodiment where the device is a bone screw 80 having a plurality of perforations 82. Perforations 82 enhance incorporation of the bone screw 80 in the host biological structure. The perforations 82 may be drill holes placed on the outer surface of the bone screw 80. Preferably, the perforations 82 should extend along the entire length of the bone screw 80, from the point 12 to the screw head 44. FIG. 20B is an exploded view of the perforations 82 on the threaded portion of the bone screw 80. The perforations 82 may be of any functionally desired size and density, although the perforations 82 should not unduly weaken the mechanical strength of the bone screw 80. Perforations are not limited to the use on screws and may also be used on other fixation devices such as rods, pins, anchors and plates to enhance incorporation of said device in the host biological structure.

Figure 21A:
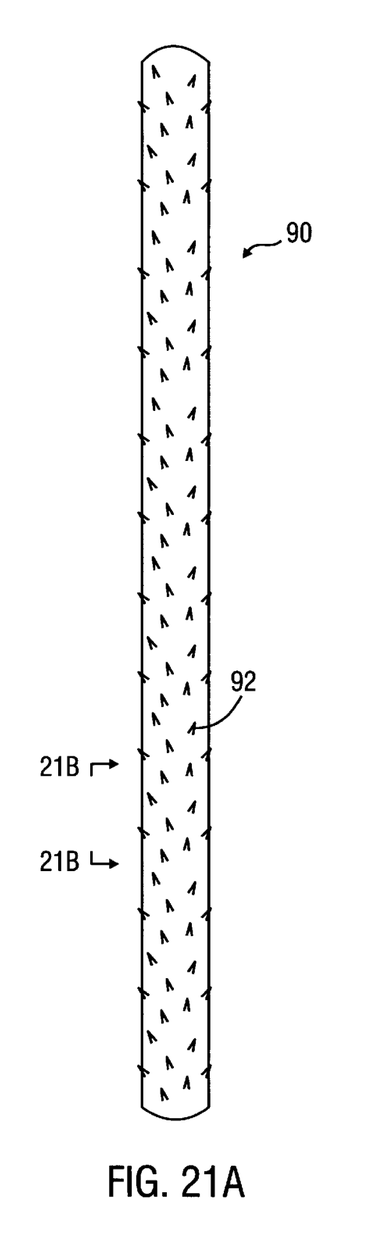
FIGS. 21A and 21B are a side view and an accompanying exploded view of a pin or rod of this invention having barbs extending along the entire length of the pin or rod.
Figure 21B:
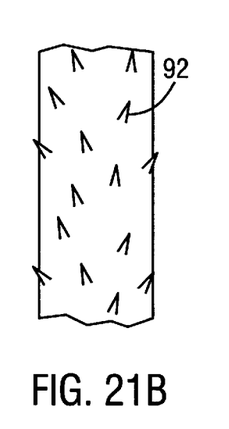
Figure 22:
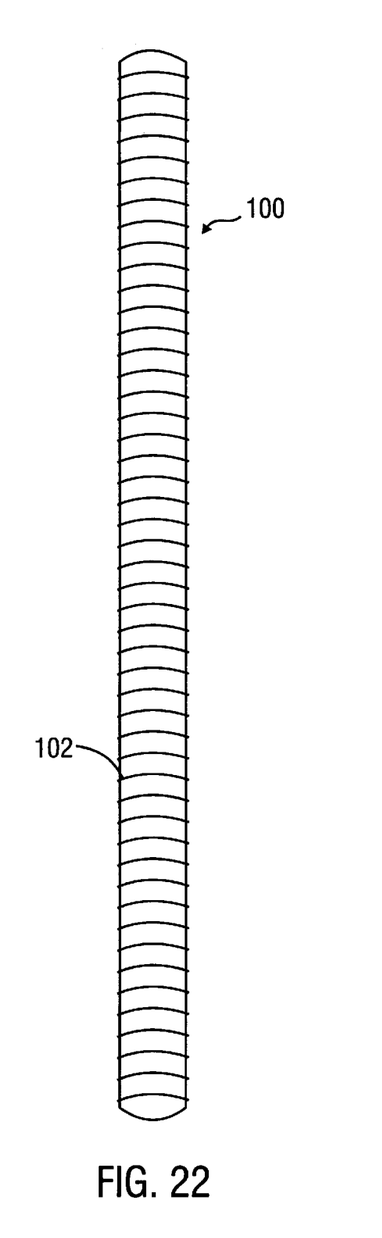
FIG. 22 is a side view of a pin or rod of this invention having threads extending along the entire length of the pin or rod.

FIGS. 21A, 21B and 22 illustrate still a further embodiment of the fixation device of this invention, a rod made of bone tissue, useful as a bone pin. The longitudinal surface of the pin or rod may be smooth, may contain barbs 92 (FIGS. 21A and 21B) or may contain threads 102 (FIG. 22). The cross section of the pin 90 and 100 may be cylindrical but is preferably elliptical. The elliptical shape provides rotational stability when inserted into a round, predrilled guidehole into a patient's bone. The pins 90 and 100 are about 1 to 10 mm in largest diameter, less in smaller diameter and from about ¼ cm to 20 cm in length. Lengths of 1 to 10 cm are preferred.

Figure 23:
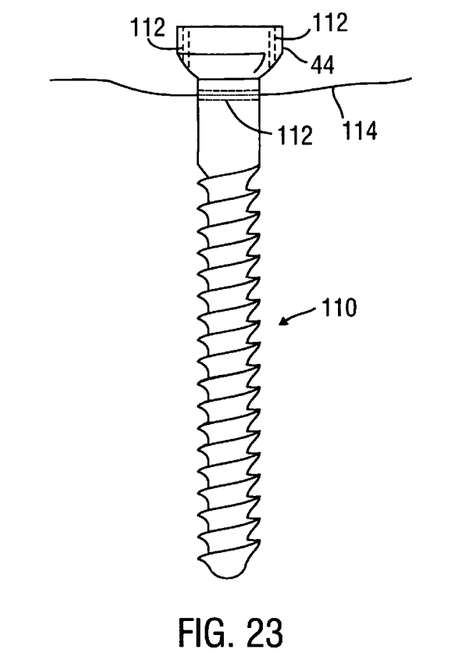
FIG. 23 is a side view of a screw of this invention having suture apertures extending through a portion of the head and the longitudinal axis of the screw. A representation of the positioning of a suture is also shown such that the suture is inserted through apertures in a fashion that avoids friction with surrounding tissue.

FIG. 23 illustrates one embodiment where the device is a bone screw 110 having at least one aperture 112, in which at least one or more of the apertures 112 is perpendicular to the longitudinal body portion. Preferable, the screw will have an aperture 112 drilled through the head so as to permit insertion of suture material at or above the level of the bone. This may involve three apertures 112 as shown in FIG. 23. The aperture 112 is sized to accommodate a suture 114 and should be of no more than about 2 mm in diameter. Another illustration of this embodiment is shown in FIG. 26.

Figures 24, 25:
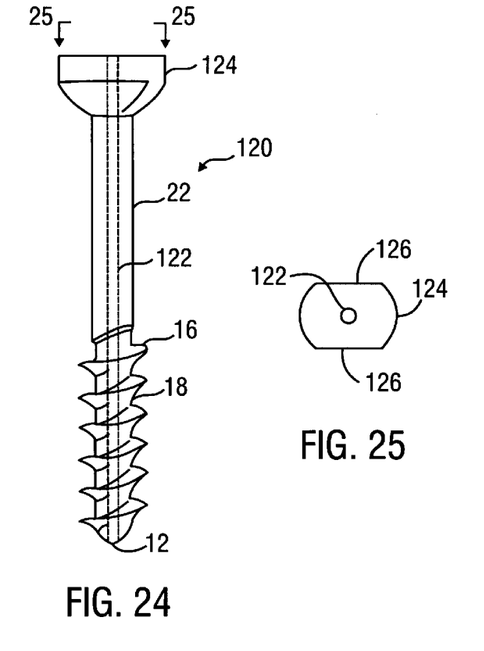
FIG. 24 is a side view of a cannulated screw of this invention having an aperture extending along the entire longitudinal axis of the screw.
FIG. 25 is a top view of the head portion of FIG. 24.

FIG. 24 illustrates a further embodiment of this invention, a cannulated screw 120 with an aperture 122 extending along the entire longitudinal axis. The aperture 122 is of the size to allow a guide means, preferably a pin or a wire, to be inserted into the cannulated screw 120. The guide means is helpful during application and insertion because it facilitates correct alignment of the cannulated screw 120 through the screw holes which are not always readily visible and will facilitate the determination of the proper length and placement of the cannulated screw 120. The cannulated screws 120 are about 12 mm in largest diameter and from about 1 to 20 cm in length. The preferred length is 1 to 10 cm. The aperture 122 is about 2 mm in largest diameter. The threads 16 are from about 0.1 to 5 mm, 0.5 to 4 mm, or preferably 1 to 3 mm point to point. The threads 16 can cover the entire screw or only part of the cannulated screw 120. The threads 16 are placed in correspondence to their end use. The aperture 122 may also be threaded or have an internal configuration that facilitates its ultimate end use.

FIG. 25 illustrates a top view of the spherical head 124 of the cannulated screw 120 with an aperture 122. The spherical screw head 124 comprises of a cylinder with flat surfaces 126 on at least two opposing sides similar to the spherical head 44 in FIGS. 7 and 14. Accordingly, the screw head may also be non-spherical with at least three flat sides (FIGS. 9–11) and with the addition of an aperture 122.

Figure 26:
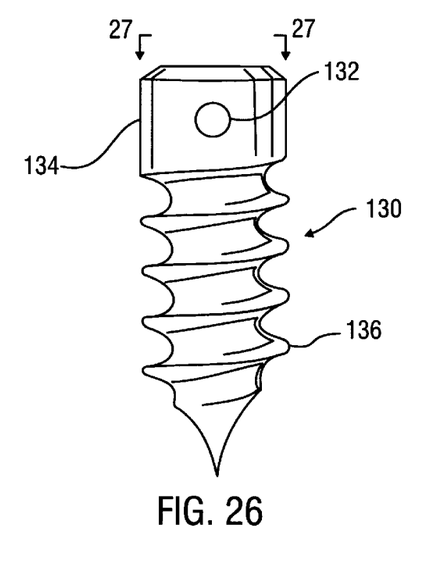
FIG. 26 is a side view of an anchor fixation device of this invention with a hole for insertion of sutures or anchoring material and FIG. 27 is a top view of the mechanism for applying rotational movement to the anchor of FIG. 26.
Figure 27:
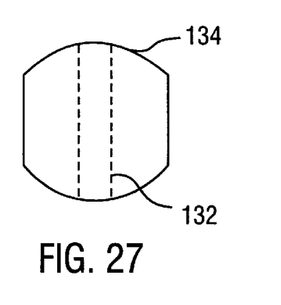

FIG. 26 illustrates still another embodiment, a bone anchor 130. Typically, the bone anchor 130 is secured to the bone of the patient by threads 136. The bone anchor 130 can be used in a variety to sizes and thread pitches depending on the patient and ultimate end use. The preferred pitch of threads 136 is 1.25 to 1.75 mm but may be shorter or longer depending on the head. Common anchor sizes include 2.7 mm×8.0 mm; 3.5 mm×10 mm; and 4.5 mm×12.0 mm (outer diameter×height). These sizes are provided by way of illustration and not limitation. The bone anchor 130 has one or more apertures 132 extending through one or more sections of the width of the bone anchor 130, typically the head 134 of the bone anchor 130. The anchor head 134 is adapted to receive a rotational tool and has at least two flat sides as shown in FIG. 27. The diameter of the head 134 will vary in proportion to the core diameter and outside diameter of the anchor threads 136. The aperture 132 is 0.01 to 2 mm, or preferably 0.7 to 1.2 mm in diameter. When the bone anchor 130 is placed into the patient's bone, the aperture 132 permits the bone anchor 130 to be used in configuration with other body repair devices such as suture thread for ligament or tendon repair and attachment to bone.

Figure 28A:
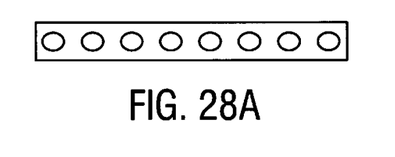
FIGS. 28A through 28I are front views of the bone plate embodiments of this invention in a variety of configurations.
Figure 28B:
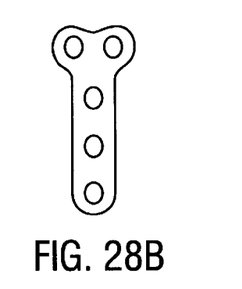
Figure 28C:
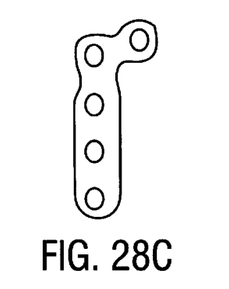
Figure 28D:
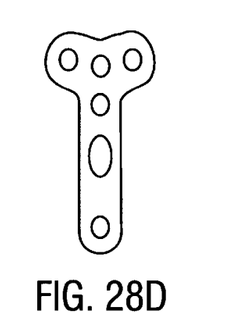
Figure 28E:
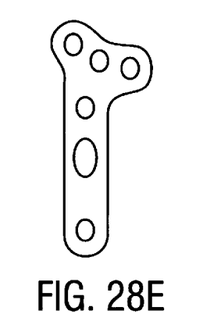
Figure 28F:
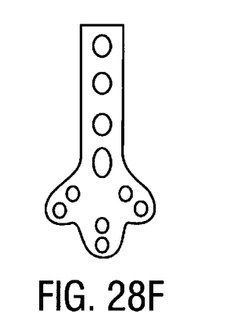
Figure 28G:
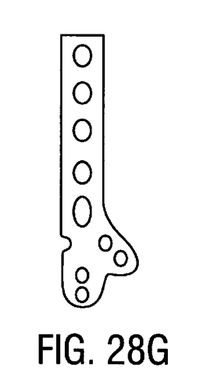
Figure 28H:
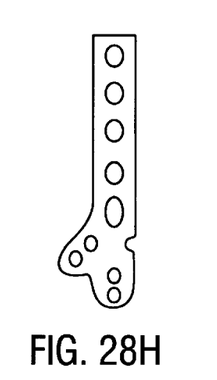
Figure 28I:
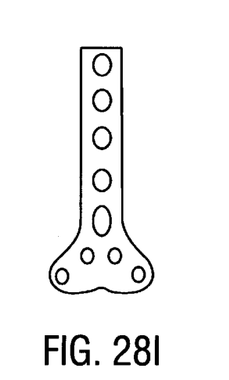

FIGS. 28A–28I illustrate still a further embodiment of the invention, bone fixation devices in the form of a bone plate. The plate can be made from one or more pieces of bone or can be molded from bone powder in combination with appropriate adhesive material. The bone plates can take a variety of forms and shapes depending on the desired end use. Typically, the bone plates are in the shape of a small—T (FIG. 28B) or an oblique —L (FIG. 28C). Other shapes may include a tubular (straight) section (FIG. 28A), a large—T (FIG. 28D), an oblique —T (FIG. 28E), a clover-leaf section (FIG. 28F) and in other shape as desired (FIGS. 28G–28I). Regardless of the shape of the bone plate, a series of small screw holes are incorporated into the plate to allow anchoring of the bone plates to the recipient surface. FIGS. 28A–28I are provided by way of illustration and not limitation.

Veterinary fixation devices may be of the same design as for human use but made from appropriate bone tissue or from human bone.

MANUFACTURE OF DEVICES

The devices of this invention are machined from bone tissue. Bone tissue, preferably sterile tissue from a bone bank, and more preferably from Musculoskeletal Transplant Foundation of New Jersey, is machined to the desired shape. In manufacturing the fixation devices, special care is needed to prevent burning or otherwise destroying the bone tissue.

If sterile tissue is not used, it is necessary that tissue, capable of sterilization be used. Accordingly, the bone fixation devices must be carefully machined using a lubricant (preferably sterile lubricant) to maintain the bone tissue surface temperature below that which causes burning or other destruction of the tissue. The lubricant must be sterile or capable of sterilization or of complete removal from the bone tissue to prevent contamination of the tissue. A suitable lubricant is sterile saline solution.

For example, a screw embodiment of this invention is made by machining cortical bone tissue, to the configuration shown in FIGS. 1, 2, 4, 5, 6 and 13. In machining it is important to keep the cutting as sharp as possible and to conduct the machining with a cooling cutting fluid, lubricant or air. Surface temperatures below about 150° C. are preferred. Special cutting jigs, as will be known to those skilled in the art of ceramic or tile cutting are appropriately used. Perforated screws, cannulated screws, bone anchors, pins and rods can be made using the same procedure, but machining to a different configuration.

Bone plates can be made from one or more pieces of bone or from bone powder and a proper adhesive. For example, when bone powder is used, the powder is adhered into the desired shape by the use of a binding agent into the powder mix. Suitable bonding agents may be absorbably polymers or resorbably glass/ceramic composites.

After machining, the bone fixation devices must be treated to sterilize them. This treatment may be the same or different as that used to treat the bone in the first instance. For example, boiling, treatment with hydrogen peroxide and/or ethylene oxide will be appropriate. The treated device may also be irradiated. Irradiation must be carried out so as not to unduly weaken the device. Suitable conditions are known to those skilled in treatment for bone graft tissue. Treatment to ensure sterility are well within the skill of the art and do not, as such, form a part of the present invention.

Veterinary bone fixation devices may be made in the same manner as described above. Sterile bone tissue may not be available but can be harvested under conditions that allow sterilization of the finished device. For example, cortical bone tissue may be harvested from horse bone tissue under clean, draped conditions, the tissue immediately frozen in liquid nitrogen and then freeze dried as with human bone. The freeze dried bone will then be used for fabrication of the device.

Use

The use of bone fixation devices made of sterile human bone will greatly facilitate healing and may help prevent infection and rejection as is experienced with metal or resorbable polymer material. Moreover, the fixation device will in fact become grafted into the drill hole used for insertion. This grafting will allow more natural knitting and healing of the drill hole used for screw or pin insertion. Further, the fixation device will not have to be removed in a subsequent operation.

The fixation devices of this invention can be used in the same manner as existing metal or polymer devices. For example, to secure a fractured long bone a hole is drilled through bone on either side of the fracture. The hole on the proximate side where the screw is to be inserted will be larger in diameter than the screw thread diameter. The hole in the bone away from the insertion point is drilled about the same diameter as the screw base diameter and tapped to accommodate the screw threads. The hole is countersunk at the insertion point to accommodate the screw head. When inserted, the screw male threads engages the tapped female threads and pulls the fractured bone tightly and securely together. It is important that the fracture be securely held in place for sufficient time to allow the bone to regenerate. Thus, the material of the screw must maintain its integrity for a time sufficient to allow regrowth of the bone through the fracture. Therefore, it is important that the fixation device be made of cortical bone. While integration is slow, it is of a similar time scale as necessary for healing of a bone fracture. Bone fracture is generally healed within three weeks to six months. If softer bone tissue is used there is the possibility that it will be absorbed and therefore lose its strength before the fracture is healed. Since freeze dried bone tissue will have a moisture content of 5% or lower, it may be desirable to soak the device in saline solution or other suitable medium to restore moisture prior to insertion. Restoration of the bone tissue moisture is desirable in bone grafting and will assist in acceptability if the bone device into the body. Pins may be inserted with a metal applicator that allows the pin to be inserted into a hole in the end of the applicator. The applicator serves to assist the surgeon in inserting the pin. Such applicators are used with Biofix™ absorbable rods. Biofix is a trademark of Biosciences, Ltd. and available from Biosciences 2 Inc. in the United States.

In one embodiment, a bone screw of this invention is used as an anchor attachment for holding bone and tendon or bone and cartilage or bone to other connective tissue in place. The screw has a small hole drilled through or just below the head and perpendicular to the length of the screw. The hole is of a diameter to accommodate a suture or other tying material. For example the hole is from 0.01 to 2 mm in diameter. The surgeon may insert his/her own suture material or it may be provided with the screw. The screw is inserted into the bone into a drilled and tapped hole and the suture used to tie a tendon or cartilage (or another bone or one splint or graft) in place. The suture may be tied off to a second suture screw or bone plug.

In another embodiment, the fixation device is a rod or pin with or without threading. If the rod or pin is used without threading, it is inserted into the bone after a track is created by a similar size metal rod or pin. It may be necessary to cut the rod or pin to size. If the rod or pin has a part that is threaded, then the rod or pin is inserted into the patient's bone up to the required length and is then cut flush with the bone. Once inserted, the rod or pin will graft to the patient's bone.

A further embodiment of the invention uses bone plates. These plates are attached to the recipient bone by bone screws. The plates are particularly useful in situations in which rigid fixation is needed.

Thus, there is disclosed in the above description and the drawings fixation devices which fully and effectively accomplish the objections of this invention. However, it will be apparent that variations and modifications of the disclosed embodiments may be made without departing from the principles of the invention or the scope of the appended claims.

What is claimed is:

1. A fixation device formed in the shape of a screw, said fixation device made of human or animal cortical bone, said fixation device being grafted into a biologically active structure, said fixation device being interactive with said structure and forming a part of said structure, said fixation device being compatible with the functional characteristics of said structure, said fixation device comprising:

a) a head portion functionally adapted to provide rotational movement to said fixation device;

b) said head portion being fixedly attached to a longitudinal body portion, said head portion being cylindrical and having a slot, said slot being perpendicular to said longitudinal body portion and adapted to receive a rotational tool; and c) said longitudinal body portion being at least partially threaded with a thread pitch of 0.5 to 3.0 mm, said longitudinal body portion having a threaded diameter ranging from 1 to 8 mm and a core diameter from 1 to 8 mm.

2. The fixation device of claim 1 wherein said slot being shaped in the form of a cruciform recess.

3. The fixation device of claim 1 wherein said slot being shaped to receive a Philip's head rotational tool.

4. The fixation device of claim 1 wherein said fixation device is adapted to be inserted into human or animal bone tissue.

5. The fixation device of claim 1 wherein the end of said fixation device opposite said head portion is a point.

6. The fixation device of claim 1 wherein said fixation device having a plurality of perforations on said longitudinal body portion.

7. The fixation device of claim 6 wherein said perforations piercing the surface of said longitudinal body and not extending through said longitudinal body.

8. The fixation device of claim 1 wherein said head portion is larger in diameter than the threaded diameter of said longitudinal body portion.

9. The fixation device of claim 8 wherein said head portion of the screw is cylindrical and has at least two flat sides.

10. The fixation device of claim 8 wherein said head portion has a head diameter in the range of 1 to 12 mm.

11. The fixation device of claim 8 wherein said head portion has at least one aperture, wherein at least one of said apertures is perpendicular to the longitudinal body portion and is of a configuration sufficient to accommodate at least one suture.

12. The fixation device of claim 8 wherein said fixation device has at least one aperture through said head portion.

13. A fixation device formed in the shape of a screw, said fixation device being adapted to be grafted into a biologically active structure, said fixation device being interactive with said structure and forming a part of said structure, said fixation device being compatible with the functional characteristics of said structure, said fixation device comprising:

a) a head portion functionally adapted to provide rotational movement to said fixation device, said head portion being larger in diameter than the longitudinal body portion, said head portion diameter ranging from about 1 to 12 mm, and said head portion being cylindrical with at least two flat sides;

b) said head portion being fixedly attached to a longitudinal body portion; and c) said longitudinal body portion including means being at least partially threaded, and said longitudinal body portion having a threaded diameter ranging from 1 to 8 mm.

14. The fixation device of claim 13 wherein said head portion is adapted to receive a rotational tool.

15. The fixation device of claim 13 wherein said head portion has a slot, said slot being perpendicular to said longitudinal body portion and adapted to receive a rotational tool.

16. The fixation device of claim 13 wherein said fixation device is adapted to be inserted into human or animal bone tissue.

17. The fixation device of claim 13 wherein said fixation device is not biologically toxic.

18. The fixation device of claim 13 wherein said fixation device is non-metallic.

19. The fixation device of claim 13 wherein said fixation device is made from human or animal cortical bone tissue.

20. The fixation device of claim 13 wherein said fixation device having a plurality of perforations on said longitudinal body portion.

21. A kit comprising: (1) a bone screw made from bone tissue, and (2) an adapter made of surgical steel having one end with a recess sized to mesh with the head of said screw and the other end having a screw head recess, sized to allow use of a driver to drive said bone screw.

22. A kit comprising: (1) a bone screw made from bone tissue, and (2) an adapter made of surgical steel having one end with a recess sized to mesh with the head of said screw and the other end having a cruciform recess, sized to allow use of a Philip's driver to drive said bone screw.

23. A bone fixation device formed in the shape of a screw with a head portion and a longitudinal body portion, said fixation device being made of human or animal cortical bone tissue, said fixation device being able to be grafted into a biologically active structure, said fixation devices becomes part of said structure and need not be removed, said fixation device comprising:

a) said head portion functionally adapted to provide rotational movement to said fixation device, said head portion being adapted to receive a rotational tool, said head portion being larger in diameter than the longitudinal body portion, said head diameter ranging from 2 to 10 mm, and said head portion being cylindrical with at least two flat sides;

b) said head portion being fixedly attached to said longitudinal body portion; and c) said longitudinal body portion being at least partially threaded with a thread pitch of 0.5 to 3.0 mm, said longitudinal body portion having a threaded diameter ranging from 1 to 8 mm and a core diameter range from 1 to 8 mm, said longitudinal body portion having at least one aperture perpendicular to said longitudinal body portion with a configuration sufficient to accommodate at least one suture, said aperture being below said head portion and above the first thread.

24. A method of making said fixation device of claim 1 comprising machining human or animal cortical bone tissue into the shape of a screw under conditions that do not allow the surface temperature of said bone tissue to exceed a temperature at which said bone tissue is burned or damaged and that allow said fixation device to be sterilized sufficiently to be acceptable to use in the fixation of living bone.

25. The method of claim 24 wherein said bone tissue is sterile prior to machining, the machining is carried out using a cooling lubricant, and said fixation device is sterilized after completion.

26. A fixation device formed in the shape of a screw, said fixation device made of human or animal cortical bone, said fixation device being grafted into a biologically active structure, said fixation device being compatible with the functional characteristics of said structure, said fixation device comprising:

a) two end portions, at least one of said end portions being adapted to provide rotational movement to said fixation device;

b) said end portions being fixedly attached to a longitudinal body portion;

c) one of said end portions formed in the shape of a cylindrical screw head and having an indentation, said indentation being perpendicular to said longitudinal body portion, said indentation being shaped to receive a rotational tool; and d) said longitudinal body portion being at least partially threaded with a thread pitch of 0.5 to 3.0, said longitudinal body portion having a thread diameter ranging from 1 to 8 mm and a core diameter range from 1 to 8 mm.

27. The fixation device of claim 26 wherein said fixation device has an aperture extending along the entire longitudinal axis, said aperture having a configuration sufficient to allow the insertion of a pin.

28. The fixation device of claim 26 wherein said fixation device has an aperture extending along the entire longitudinal axis, said aperture having a configuration sufficient to allow the insertion of a wire.

29. The fixation device of claim 26 wherein said indentation being shaped to receive a Philip's head rotational tool.

30. The fixation device of claim 26 wherein said indentation being shaped in the form of a cruciform recess.

31. The fixation device of claim 26 wherein said fixation device has a length of 1 to 10 cm.

32. The fixation device of claim 26 wherein said fixation device having a plurality of perforations on said longitudinal body portion.

33. A fixation device formed in the shape of a screw, said fixation device being adapted to be grafted into a biologically active structure, said fixation device being interactive with said structure and forming a part of said structure, said fixation device being compatible with the functional characteristics of said structure, said fixation device comprising:

a) two end portions, at least one of said end portions being able to receive a rotational tool to provide rotational movement to said fixation device;

b) said end portions being fixedly attached to a longitudinal body portion; and c) said longitudinal body portion, wherein said longitudinal body portion has an aperture extending along the entirety of said longitudinal body portion, said aperture having a configuration sufficient to allow the insertion of a pin, said longitudinal body portion having threads extending from a region above one of said end portions to a region below other said end portion.

34. A fixation device formed in the shape of a screw, said fixation device being made of human or animal cortical bone tissue, said fixation device being able to be grafted into a biologically active structure, said fixation device becoming a part of said structure and need not be removed from said biologically active structure, said fixation device comprising:

a) two end portions, at least one of said end portions being able to receive a rotational tool to provide rotational movement to said fixation device, at least one of said ends being cylindrical and having only two flat sides;

b) said end portions being fixedly attached to a longitudinal body portion; and c) said longitudinal body portion which has an aperture extending along the entirety of said longitudinal body portion, said aperture having a configuration sufficient to allow the insertion of a pin, said longitudinal body portion having threads extending from a region about one of said ends to a region below other said end, wherein the thread diameter is about 3.0 mm, the thread pitch is about 1.25, and the core diameter is about 1.9 mm.

35. A method of making said fixation device of claim 34 comprising machining human or animal cortical bone tissue into the shape of a screw under conditions that do not allow the surface temperature at which bone tissue is burned or damaged and that allow said fixation device to be sterilized sufficiently to be acceptable to use in the fixation of living bone.

36. The method of claim 35 wherein said bone tissue is sterile prior to machining, the machining is carried out using a cooling lubricant, and said fixation device is sterilized after completion.

37. A fixation device in the shape of a pin, said fixation device made of human or animal cortical bone, said fixation device being adapted to be grafted into a biologically active structure, said fixation device being interactive with said structure and forming a part of said structure, said fixation device being compatible with the functional characteristics of said structure, said fixation device comprising:

a) two end portions being fixedly attached to a longitudinal body portion;

b) said longitudinal body portion including a means for fixedly retaining at least a portion of said longitudinal body portion in said biologically active structure; and c) said longitudinal body portion is elliptical.

38. A fixation device in the shape of a pin, said fixation device made of human or animal cortical bone, said fixation device being adapted to be grafted into a biologically active structure, said fixation device being interactive with said structure and forming a part of said structure, said fixation device being compatible with the functional characteristics of said structure, said fixation device comprising:

a) two end portions being fixedly attached to a longitudinal body portion;

b) said longitudinal body portion including a means for fixedly retaining at least a portion of said longitudinal body portion in said biologically active structure; and c) said longitudinal body portion having a plurality of barbs extending from a region above one of said end portions to a region below other said end portion.

39. A fixation device in the form of an screw adapted to be grafted into a biologically active structure, said fixation device being compatible with the functional characteristics of said structure, said fixation device comprising:

a) a head portion functionally adapted to provide rotational movement to said fixation device, said head portion having at least one aperture extending through the width of said head portion;

b) said head portion being fixedly attached to a longitudinal body portion; and c) said longitudinal body portion being at least partially threaded.

40. The fixation device of claim 39 wherein said head portion is adapted to receive a rotational tool.

41. The fixation device of claim 39 wherein said head portion has at least two flat sides.

42. The fixation device of claim 39 wherein said fixation device is made of human or animal cortical bone tissue.

43. The fixation device of claim 39 wherein said fixation device is inserted into human or animal bone tissue.

44. The fixation device of claim 39 wherein said fixation device is not biologically toxic.

45. The fixation device of claim 39 wherein said fixation device is non-metallic.

46. The fixation device of claim 39 wherein said fixation device having a plurality of perforations on said longitudinal body portion.

47. A fixation device adapted to be grafted into a biologically active structure, said fixation device being compatible with the functional characteristics of said structure, said fixation device made of human or animal cortical bone, said fixation device comprising:

a) a plate having a series of holes; and b) said plate is in the shape of an oblique-L.

48. A fixation device adapted to be grafted into a biologically active structure, said fixation device being compatible with the functional characteristics of said structure, said fixation device made of human or animal cortical bone, said fixation device comprising:

a) a plate having a series of holes; and b) said plate is in the shape of a small-T.

49. A fixation device adapted to be grafted into a biologically active structure, said fixation device being compatible with the functional characteristics of said structure, said fixation device made of human or animal cortical bone, said fixation device comprising:

a) a plate having a series of holes; and b) said plate is in the shape of a clover leaf.

50. The fixation device of claim 1 wherein said fixation device has an aperture extending along the entire longitudinal axis, said aperture having a configuration sufficient to allow the insertion of a pin.

51. The fixation device of claim 1 wherein said fixation device has an aperture extending along the entire longitudinal axis, said aperture having a configuration sufficient to allow the insertion of a wire.

52. The fixation device of claim 13 wherein said fixation device has an aperture extending along the entire longitudinal axis, said aperture having a configuration sufficient to allow the insertion of a pin.

53. The fixation device of claim 13 wherein said fixation device has an aperture extending along the entire longitudinal axis, said aperture having a configuration sufficient to allow the insertion of a wire.

54. The fixation device of claim 13 wherein said head portion being cylindrical with only two flat sides.

55. The fixation device of claim 13 wherein said head portion being cylindrical with only three flat sides.

56. The fixation device of claim 13 wherein said head portion having at least one aperture extending through the width of said head portion.

57. The fixation device of claim 13 wherein said longitudinal body portion having at least one aperture perpendicular to said longitudinal body portion, said head portion having at least one aperture, wherein at least one of said apertures of said head portion is parallel to the longitudinal body portion and is of a configuration sufficient to accommodate at least one suture.

58. The fixation device of claim 20 wherein said perforations piercing the surface of said longitudinal body and not extending through said longitudinal body.

59. The fixation device of claim 23 wherein said head portion being cylindrical with only two flat sides.

60. The fixation device of claim 23 wherein said head portion being cylindrical with only three flat sides.

61. The fixation device of claim 23 wherein said head portion has at least one aperture, wherein at least one of said apertures of said head portion is parallel to the longitudinal body portion and is of a configuration sufficient to accommodate at least one suture.

62. The fixation device of claim 23 wherein said longitudinal body portion having a plurality of perforations.

63. The fixation device of claim 62 wherein said perforations piercing the surface of said longitudinal body and not extending through said longitudinal body.

64. The fixation device of claim 26 wherein said longitudinal body portion having at least one aperture perpendicular to said longitudinal body portion, said head portion having at least one aperture, wherein at least one of said apertures of said head portion is parallel to the longitudinal body portion and is of a configuration sufficient to accommodate at least one suture.

65. The fixation device of claim 32 wherein said perforations piercing the surface of said longitudinal body and not extending through said longitudinal body.

66. The fixation device of claim 34 wherein said head portion being cylindrical with three flat sides.

67. The fixation device of claim 39 wherein said head portion being cylindrical with only two flat sides.

68. The fixation device of claim 39 wherein said head portion being cylindrical with only three flat sides.

69. The fixation device of claim 46 wherein said perforations piercing the surface of said longitudinal body and not extending through said longitudinal body.

70. A fixation device adapted to be grafted into a biologically active structure, said fixation device being compatible with the functional characteristics of said structure, said fixation device made of human or animal cortical bone, said fixation device comprising:

a) a plate having a series of holes; and b) said human or animal cortical bone is mineralized.

71. A method of making a fixation device in the shape of a pin, said fixation device made of human or animal cortical bone tissue, said fixation device being adapted to be grafted into a biologically active structure, said fixation device being interactive with said structure and forming a part of said structure, said fixation device being compatible with the functional characteristics of said structure, said fixation device having two end portions being fixedly attached to a longitudinal body portion, said longitudinal body portion including a means for fixedly retaining at least a portion of said longitudinal body portion in said biologically active structure, the method comprising:

a) sterilizing said human or animal cortical bone tissue;

b) machining said human or animal cortical bone tissue into the shape of a pin with a cooling lubricant under conditions that do not allow the surface temperature at which bone tissue is burned or damaged and that allow said fixation device to be sterilized sufficiently to be acceptable to use in the fixation of living bone;

c) sterilizing the fixation device after said machining.

* * * * *